United States Patent [19]
Oren et al.

[11] Patent Number: 5,906,629
[45] Date of Patent: May 25, 1999

[54] ARTHROSCOPIC SURGICAL APPARATUS

[75] Inventors: Ran Oren; Dan Moor, both of Asherat, Israel

[73] Assignee: T.A.G. Medical Products Ltd., Kibbutz Gaaton, Israel

[21] Appl. No.: 08/863,711

[22] Filed: May 27, 1997

[51] Int. Cl.$^6$ .......................... A61B 17/28; A61B 17/32; A61B 17/34
[52] U.S. Cl. .......................... 606/205; 606/174; 606/185
[58] Field of Search .......................... 606/1, 151, 157, 606/159, 167, 174, 205–211, 185, 184; 264/249

[56] References Cited

U.S. PATENT DOCUMENTS

| | | | |
|---|---|---|---|
| 3,740,779 | 6/1973 | Rubricuis | 606/167 |
| 4,522,206 | 6/1985 | Whipple et al. | 606/79 |
| 4,671,916 | 6/1987 | Hamas | 264/249 |
| 5,578,052 | 11/1996 | Koros et al. | 606/174 |
| 5,665,105 | 9/1997 | Furnish et al. | 606/1 |

*Primary Examiner*—Glenn K. Dawson
*Attorney, Agent, or Firm*—Mark M. Friedman

[57] ABSTRACT

An arthroscopic surgical apparatus for a minimum invasive surgery of the joint is provided. The apparatus includes: (a) a shaft member for insertion into a patient's body, the shaft member featuring a groove for receiving an operating rod therein; (b) a movable operating rod received within the shaft member; (c) a first jaw member connected to the shaft member; and a second jaw member connected to the operating rod, the jaw members for operating a body portion of a patient, the first and second jaw members being interconnected by means of a jaw pivot; (d) a first handle connected to the shaft member; and a second handle connected to the operating rod, the handles for holding by a user, the first and second handles are inter-connected by means of a handle pivot. The apparatus preferably includes a blocking member for determining a maximal opening of the first and second handles, thereby determining a maximal opening of the first and second jaw members. The second handle is preferably connected to the operating rod by means of a readily replaceable shear pin received within two accommodating members such as screws. A color-coded identification system is provided wherein each tip member configuration is marked by a characteristic hand color and each shaft member configuration is marked by a characteristic knob color.

14 Claims, 4 Drawing Sheets

ARTHROSCOPIC SURGICAL APPARATUS

FIELD AND BACKGROUND OF THE INVENTION

The present invention relates to an arthroscopic surgical apparatus and, more particularly to a surgical apparatus which enables a surgeon to safely, conveniently and efficiently conduct a minimum-invasive surgery of a patient's joint.

Arthroscopic surgical instruments such as hook punches, scissors and grasping forceps are well known in the art. However, the prior art fails to provide an arthroscopic surgical instrument having a mechanical means for assisting the surgeon to avoid accidental scratching of tissues adjacent the treated site. Rather, the accuracy of such prior art mainly depends on the manual dexterity and skills of the surgeon.

Further, the prior art provides arthroscopic surgical instruments having a shear pin for restricting the maximal load on the operating tip of the instrument. Such a shear pin is designed to break under a predetermined overload, thereby preventing breaking of the operating tip within the patient's body. However, the shear pin provided by such prior art is substantially fixed within the surgical instrument. Thus, when such a shear pin breaks it is necessary to disassemble other parts of the surgical instrument for replacing the shear pin. Such procedure is time consuming and cannot be carried out during operation.

Further, the existing surgical instruments fail to provide a means for assisting the medical team to immediately identify the type of surgical tool to be used so as to facilitate handling of various types of similar-looking tools during operation.

There is thus a widely recognized need for, and it would be highly advantageous to have, an arthroscopic surgical apparatus which enables a medical team to safely, conveniently and efficiently conduct an arthroscopy surgery. Specifically, there is a widely recognized need for, and it would be highly advantageous to have, an arthroscopic surgical apparatus which includes a mechanical means such as a stop screw for assisting the surgeon to avoid accidental scratching of tissues adjacent a treated site. There is further a recognized need for an arthroscopic surgical apparatus which includes a readily replaceable shear pin which can be easily replaced by the medical team upon breaking. There is further a recognized need for an arthroscopic surgical apparatus which includes a means for immediately identifying the type of surgical tool to be used by a surgeon, thereby facilitating handling of several similar looking tools and thus improving the efficiency of the surgical procedure.

SUMMARY OF THE INVENTION

According to the present invention there is provided an arthroscopic surgical apparatus, comprising: (a) a shaft member for insertion into a patient's body, the shaft member featuring a groove for receiving an operating rod therein; (b) a movable operating rod received within the shaft member; (c) a first jaw member connected to the shaft member; and a second jaw member connected to the operating rod, the jaw members for operating a body portion of a patient, the first and second jaw members being inter-connected by means of a jaw pivot; (d) a first handle connected to the shaft member; and a second handle connected to the operating rod, the handles for holding by a user, the first and second handles being inter-connected by means of a handle pivot.

According to further features in preferred embodiments of the invention described below, the apparatus includes a blocking member for determining a maximal opening of the first and second handles, thereby determining a maximal opening of the first and second jaw members. The blocking member may be an adjustable stop screw and may be placed on the first handle, or alternatively on the second handle.

According to still further features of the invention described below, the second handle is preferably connected to the operating rod by means of a readily replaceable shear pin received within two accommodating members such as screws. Such configuration eliminates the need to disassemble other portions of the apparatus upon breaking of the shear pin.

According to the present invention there is further provided a surgical apparatus, comprising: (a) at least one handle for holding by a user, the at least one handle including a marker; (b) a tip member for operating a body portion of a patient, the tip member featuring a specific configuration, such that the specific configuration of the tip member is identified by the marker. The marker may be a colored surface on the at least one handle, such that the configuration of the tip member is identified by the color of the surface. The tip member may preferably feature a configuration of a cutting member, a punching member, or a grasping member.

Further, according to the present invention the is provided a surgical apparatus, comprising: (a) at least one handle for holding by a user, the at least one handle including a marker; (b) a shaft member for insertion into a body portion of a patient, the shaft member featuring a specific configuration, such that the specific configuration of the shaft member is identified by the marker. The marker may be a colored knob, such that the configuration of the shaft member is identified by the color of the knob. The shaft member may includes at least one bending.

The present invention successfully addresses the shortcomings of the presently known configurations by providing an arthroscopic surgical apparatus which enables a medical team to safely, conveniently and efficiently conduct an arthroscopy surgery. Specifically, the present invention addresses the shortcomings of the presently known configurations by providing a mechanical means such as a stop screw for assisting the surgeon to avoid accidental scratching of tissues adjacent a treated site. Further, the present invention addresses the shortcomings of the presently known configurations by providing a readily replaceable shear pin which can be easily replaced by the medical team upon breaking. Further, the present invention addresses the shortcomings of the presently known configurations by providing a means for immediately identifying the type of surgical tool to be used by a surgeon, thereby facilitating handling of several similar looking tools and thus improving the efficiency of the surgical procedure.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of an arthroscopic surgical apparatus for a minimum-invasive surgery of a joint.

The principles and operation of a surgical apparatus according to the present invention may be better understood with reference to the drawings and the accompanying description.

Figure 1:
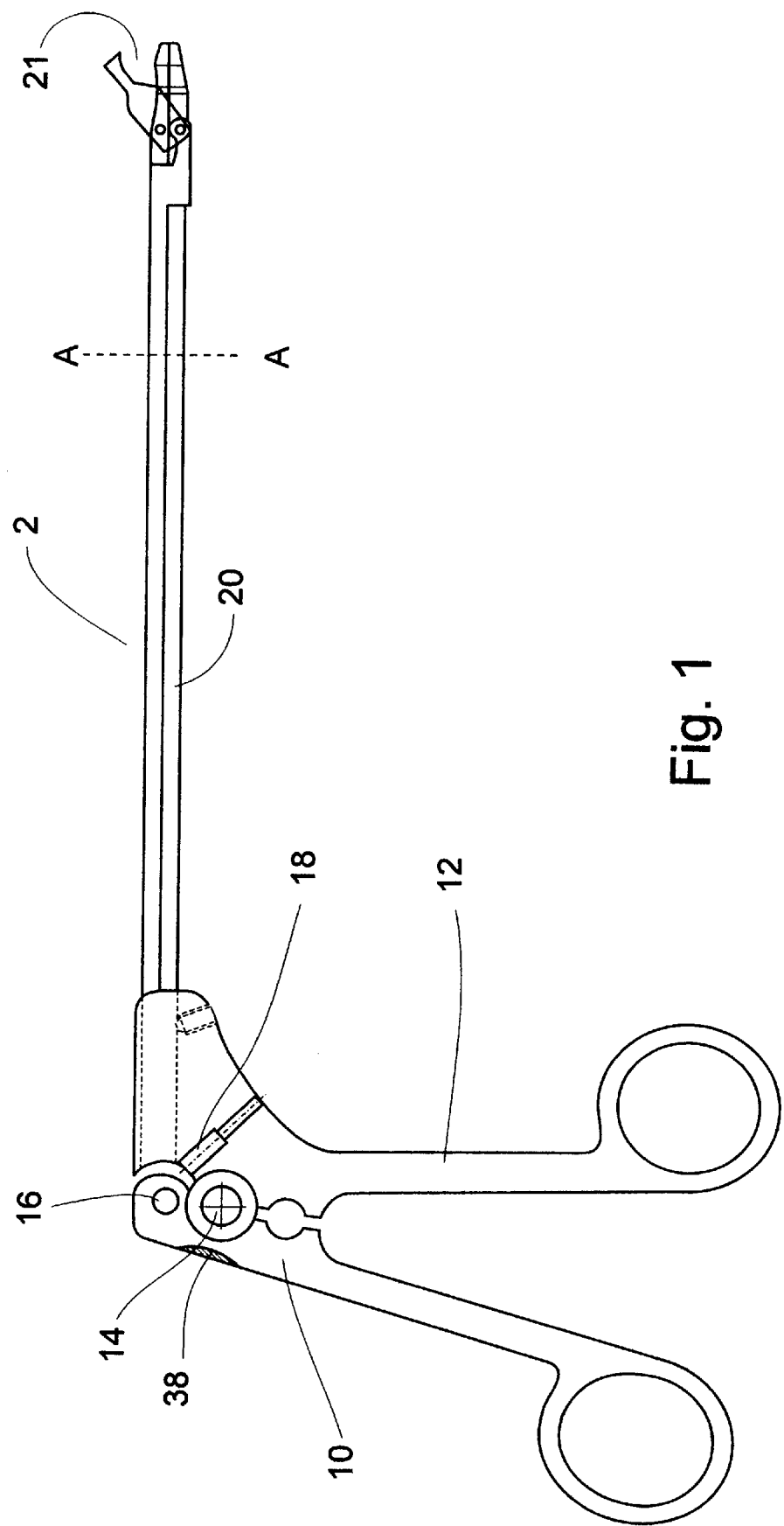
FIG. 1 is a schematic illustration of a surgical apparatus according to the present invention.
Figure 2:
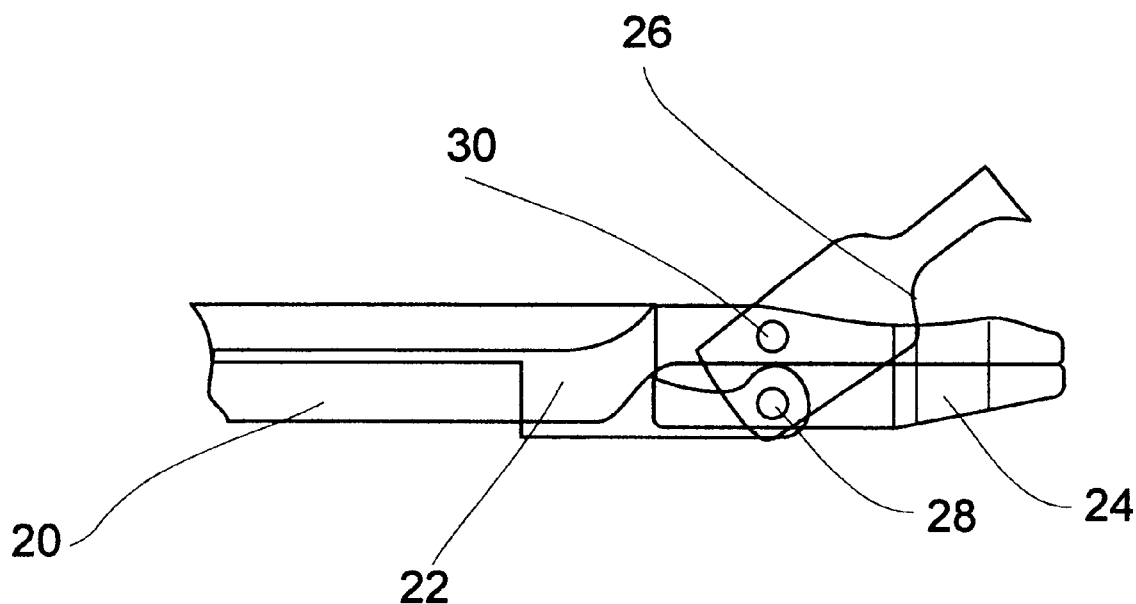
FIG. 2 is a schematic illustration of a tip portion of a surgical apparatus according to the present invention.
Figure 3:
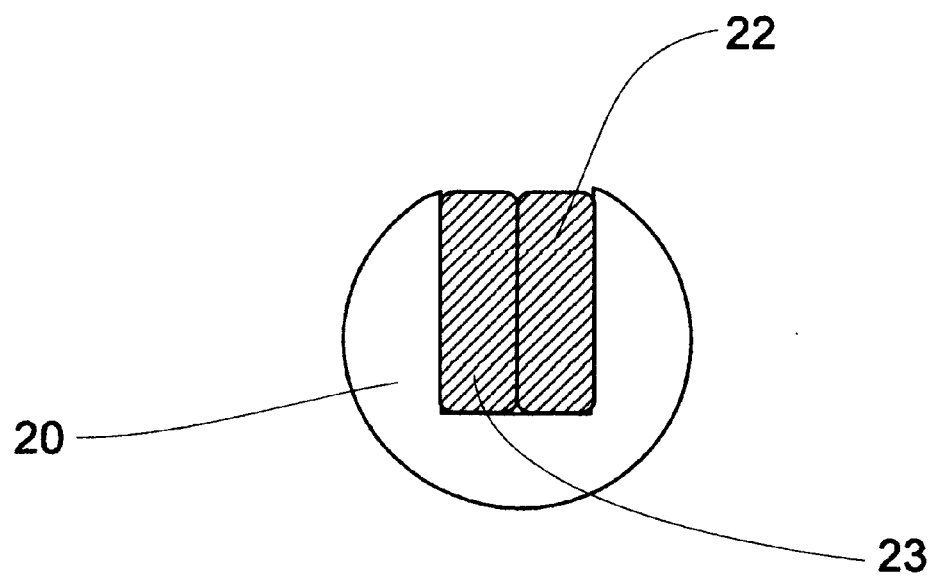
FIG. 3 is a transverse sectional view along line A—A in FIG. 1.

Referring now to the drawings, FIGS. 1–3 illustrate a surgical apparatus according to the present invention. As shown in the figures, the surgical apparatus 2 preferably includes a shaft member 20 for insertion into a patient's joint, a tip member 21 for operating the joint, and first and second handles 10 and 12 for holding the apparatus. As shown In FIG. 3, shaft member 20 preferably features an open groove 23 passing through its entire length for accommodating an operating rod 22 therein. Preferably, operating rod 22 features a rectangular shape.

As shown in FIG. 2, tip member 21 preferably includes a stationary jaw member 24 and a movable jaw member 26. Stationary jaw member 24 is preferably made as an integral part of shaft member 20. Preferably, shaft member 20 and jaw member 24 are made of a solid hardened stainless steel. As shown in the figure, movable jaw member 26 is preferably connected to stationary jaw member 24 by means of a first pivot 30, and to operating rod 22 by means of a second pivot 28. Thus, a shift of operating rod 22 within shaft member 20 towards stationary jaw member 24 results in a movement of movable jaw member 26 with relation to stationary jaw member 24 and in opening of the jaws.

As shown in FIG. 1, first handle 10 is connected to operating rod 22, and second handle 12 is connected to shaft member 20. First and second handles 10 and 12 are interconnected by means of a main pivot 14. Thus, an opening movement of handle 10 with relation to handle 12 results in a shift of operating rod 22 within shaft member 20 towards tip member 21, which in turn results in opening movement of movable jaw 26 with relation to stationary jaw 24.

An apparatus according to the present invention preferably allows a wide opening of the jaws so as to grip thick tissue sections.

Figure 4:
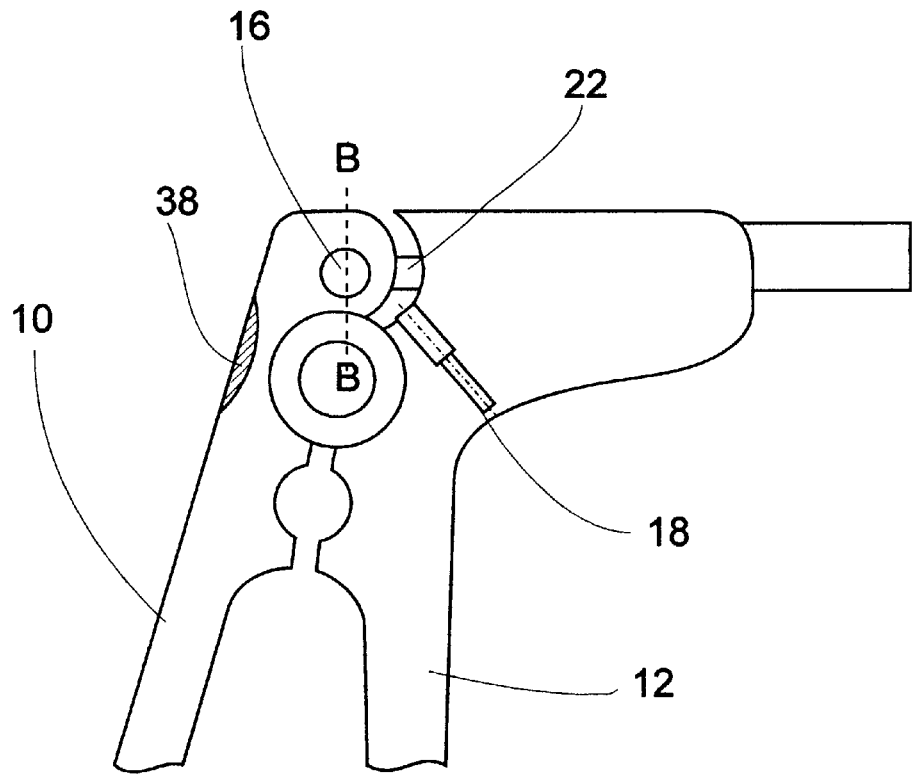
FIG. 4 is an enlarged view of a portion of the apparatus shown in FIG. 1 including a stop screw and a shear pin according to the present invention.

Further, an apparatus according to the present invention preferably features an adjustable jaw opening. As shown in FIG. 4, apparatus 2 may include an adjustable blocking member 18 such as a stop screw for determining the maximal opening of handles 10 and 12, thereby determining the maximal opening of jaws 24 and 26. Such a restriction of the maximal opening of jaws 24 and 26 prevents accidental scratching of tissue surfaces adjacent the treated site, particularly when working within tight spaces of the joint. Blocking member 18 is adjusted by the surgeon according to the specific type of surgery and the dimensions of the treated patient.

Adjustable blocking member 18 is preferably placed on handle 12. Alternatively, blocking member 18 may be placed on handle 10.

Figure 5:
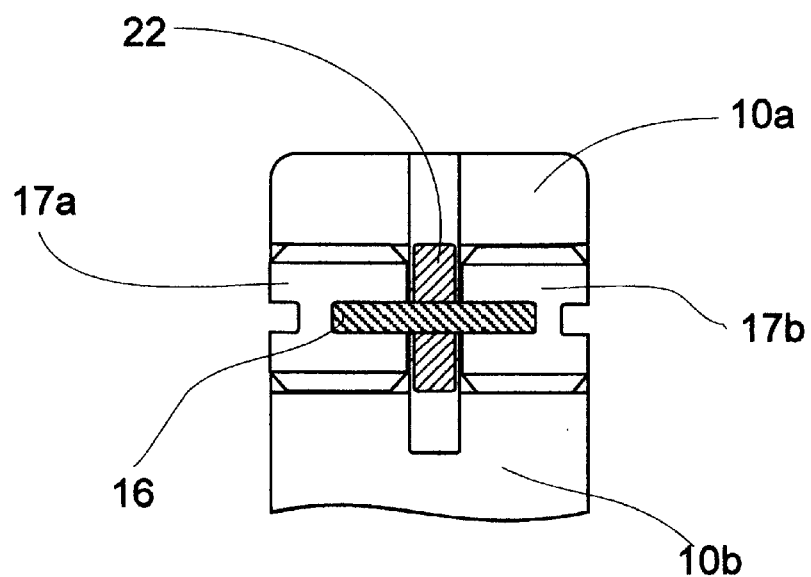
FIG. 5 is a transverse sectional view along line B—B in FIG. 4.

As shown in FIGS. 4 and 5, an apparatus according to the present invention preferably includes a readily replaceable shear pin 16. Shear pin 16 is preferably designed to yield at about 60% of the stress which would damage the components of tip 21, and thus protects against overloading of tip 21. Thus, the danger of damaged, broken, or loose pieces remaining within the treated joint is avoided.

As shown in FIG. 5, shear pin 16 is preferably received within two opposed readily replaceable accommodating members 17a and 17b. Accommodating members 17a and 17b may be screws. Thus, upon breaking, shear pin 16 can be easily replaced by the medical team simply by removing accommodating members 17a and 17b and introducing a spare assembly of shear pin 16 (and accommodating members 17a and 17b?).

Such configuration of an easily replaceable shear pin is advantageous over present configurations including substantially fixed shear pin since it eliminates the need to disassemble other components of the surgical apparatus upon breaking of the shear pin.

Figure 6:
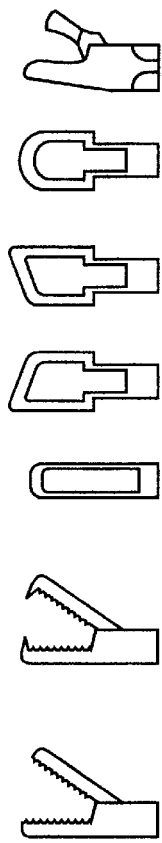
FIG. 6 illustrates several configurations of a tip portion of a surgical apparatus according to the present invention.

As shown in FIG. 6, tip portion 21 may feature any configuration adapted for tissue cutting, punching, grasping, and the like.

Figure 7:
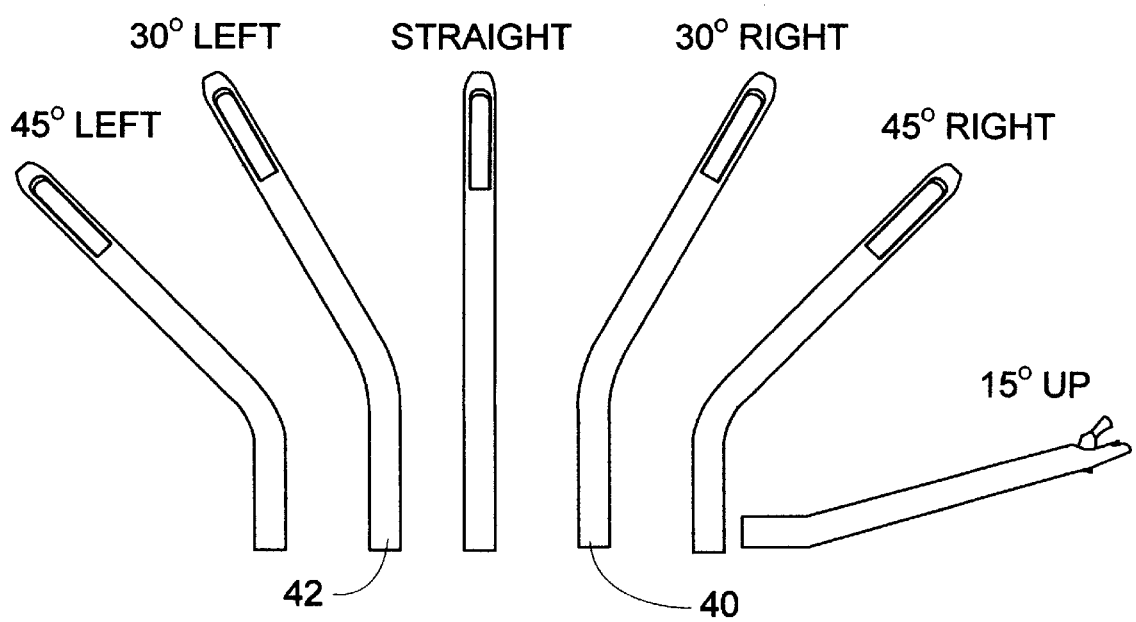
FIG. 7 illustrates several configurations of a shaft portion of a surgical apparatus according to the present invention.

Further, as shown in FIG. 7, shaft member 20 may feature various shapes for allowing access to different portions of the joint. For example, shaft member 20 may feature a shaft-bend 40 so as to allow access to substantially right portions of the treated joint. Alternatively, shaft member 20 may feature a shaft-bend 42, so as to allow access to substantially left portions of the treated joint.

When conducting a surgery, it is necessary to keep a set of different embodiments of the surgical apparatus in the operating room, each embodiment having a distinct combination of a particular tip member configuration and a particular shaft member configuration. According to the present invention there is provided a differentiation means for easily identifying each embodiment.

Specifically, each embodiment may be identified by a specific combination of two markers: a first marker for a identifying a tip configuration; and a second marker for identifying a shaft configuration. For example, a differentiation means for easily identifying the particular configuration of tip member 12 may be a characteristic hand color. A differentiation means for easily identifying the particular configuration of shaft member 20 may be a colored knob 38 placed on handle 10, the knob having a characteristic color.

Thus, according to the present invention there is provided a color-coded identification system wherein each tip member configuration is marked by a characteristic hand color and each shaft member configuration is marked by a characteristic knob color. Such identification system allows the medical team to readily select the appropriate embodiment without the need to look at details, thereby improving the efficiency of the surgical procedure.

When using a surgical apparatus according to the present invention, the surgeon selects an embodiment having a desired tip configuration and a desired shaft configuration according to the color of handles 10 and 12 and the color of knob 38, respectively.

He then sets adjustable blocking member 18 so as to determine the maximal opening of handles 10 and 12, and therefore the maximal opening of jaws 24 and 26.

The surgeon then introduces shaft member 20 through a small portal into the patient's joint, and opens handles 10 and 12 so as to cut, punch or grasp a tissue section by means of jaws 24 and 26.

In the event that shear pin 16 breaks due to overloading, it is easily replaced by removing accommodating members 17a and 17b and introducing a spare assembly of accommodating members and a shear pin.

While the invention has been described with respect to a limited number of embodiments, it will be appreciated that many variations, modifications and other applications of the invention may be made.

What is claimed is:

1. A surgical apparatus, comprising:
   (a) a shaft member for insertion into a patient's body, said shaft member featuring a groove for receiving an operating rod therein;
   (b) a moveable operating rod received within said shaft member;
   (c) a first jaw member connected to said shaft member; and a second jaw member connected to said operating rod, said jaw members for operating on a body portion of a patient, said first and second jaw members being inter-connected by means of a jaw pivot; and
   (d) a first handle connected to said shaft member; and a second handle connected to said operating rod by means of a readily replaceable pin, said shear pin received within a pair of readily replaceable accommodating members, said handles for holding by a user, said first and second handles being inter-connected by means of a handle pivot.

2. The apparatus of claim 1, wherein at least one of said accommodating members is a screw.

3. The apparatus of claim 1, wherein said apparatus is an arthroscopic surgical apparatus.

4. The apparatus of claim 1, wherein said shaft member features at least one bending.

5. A surgical apparatus as recited in claim 1, further comprising:
   (a) said at least one handle including a marker;
   (b) a tip member for operating on a body portion of a patient, said tip member featuring a specific configuration,
   such that said specific configuration of said tip member is identified by said marker.

6. The apparatus of claim 5, wherein said marker is a colored surface on said at least one handle, and said configuration of said tip member is identified by the color of said surface.

7. The apparatus of claim 5, wherein said tip member is selected from the group consisting of:
   (a) a cutting member;
   (b) a punching member; and
   (c) a grasping member.

8. A surgical apparatus as recited in claim 1, further comprising:
   (a) said at least one handle including a marker;
   (b) a shaft member for insertion into a body portion of a patient, said shaft member featuring a specific configuration,
   such that said specific configuration of said shaft member is identified by said marker.

9. The apparatus of claim 8, wherein said marker is a colored knob, and said configuration of said shaft member is identified by the color of said knob.

10. The apparatus of claim 8, further including a blocking member for determining a maximal opening of said first and second handles, thereby determining a maximal opening of said first and second jaw members.

11. The apparatus of claim 10, wherein said blocking member is placed on said first handle.

12. The apparatus of claim 10, wherein said blocking member is placed on said second handle.

13. The apparatus of claim 10, wherein said blocking member is a stop screw.

14. The apparatus of claim 10, wherein said blocking member is adjustable.

* * * * *